United States Patent [19]

Bott et al.

[11] Patent Number: 4,987,270
[45] Date of Patent: Jan. 22, 1991

[54] PREPARATION OF 3-ARYLISOBUTYL ALCOHOLS

[75] Inventors: Kaspar Bott, Mannheim; Herwig Hoffman, Frankenthal; Walter Scheidmeir, Limburgerhof, all of Fed. Rep. of Germany

[73] Assignee: BASF Aktiengesellschaft, Ludwigshafen, Fed. Rep. of Germany

[21] Appl. No.: 397,883

[22] Filed: Aug. 23, 1989

[30] Foreign Application Priority Data

Sep. 3, 1988 [DE] Fed. Rep. of Germany ....... 3830019

[51] Int. Cl.$^5$ ...................... C07C 29/34; C07C 27/00
[52] U.S. Cl. ...................... 568/905.000; 568/715.000; 568/813.000; 568/826.000; 568/902
[58] Field of Search .................. 568/715.000, 826.000, 568/834.000, 813.000, 804.000, 902.000, 905.000

[56] References Cited

U.S. PATENT DOCUMENTS

| | | | |
|---|---|---|---|
| 2,457,866 | 1/1949 | Carter | 568/715 |
| 2,645,667 | 7/1953 | Burgoyne | 568/715 |
| 3,119,880 | 1/1964 | Kollar et al. | 568/715 |
| 3,328,470 | 6/1967 | Poe | 568/715 |
| 3,479,412 | 11/1969 | Pregaglia et al. | 568/715 |
| 3,514,493 | 5/1970 | Pregalia et al. | 568/715 |
| 3,860,664 | 1/1975 | Yates | 568/715 |
| 3,862,944 | 1/1975 | Yates | 568/715 |
| 4,648,984 | 3/1987 | Krause et al. | 252/174.22 |
| 4,849,401 | 7/1989 | Friedrich et al. | 568/715 |

FOREIGN PATENT DOCUMENTS

| | | | |
|---|---|---|---|
| 0227057 | 7/1987 | European Pat. Off. | 568/715 |
| 1443666 | 10/1968 | Fed. Rep. of Germany | 568/715 |
| 8607352 | 12/1986 | World Int. Prop. O. | 252/174.22 |

OTHER PUBLICATIONS

Ullmann's Encyclopedia of Industrial Chemistry, vol. A1, p. 343.

Angew. Chem. 92 (1980), pp. 176–181, esp.179, Von Walter Himmele et al.

Houben-Weyl, Methoden der Organischen Chemie, 4. Auflauge, VI/1b Georg-Thieme-Verlap, Stuttgart, New York, 1984, pp. 645–652.

Primary Examiner—Werren B. Lone
Attorney, Agent, or Firm—Oblon, Spivak, McClelland, Maier & Neustadt

[57] ABSTRACT

3-Arylisobutanols of the general formula I

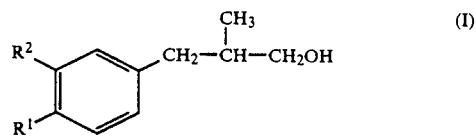

where $R^1$ and $R^2$ are each hydrogen or an alkyl or cyclo-alkyl radical of not more than 8 carbon atoms, preferably alkyl of 1 to 4 carbon atoms, are prepared by a process in which an arylcarbinol of the general formula II

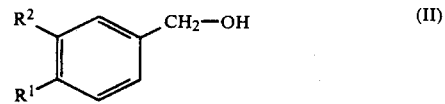

is reacted with n-propanol in the presence of a catalytic amount of an alkali metal hydroxide or an alkali metal alcoholate at from 250° to 350° C. in a closed reaction vessel.

The process is of particular importance for the preparation of 3-arylisobutanols of the formula I, where $R^1$ is alkyl of 1 to 4 carbon atoms and $R^2$ is hydrogen. The p-methyl-, p-isopropyl- and p-tert-butyl-phenylisobutanols obtained here in very good selectivity are useful intermediates for the desirable scents jasmorange, cyclamen aldehyde and Lysmeral® (Lilial®).

6 Claims, No Drawings

PREPARATION OF 3-ARYLISOBUTYL ALCOHOLS

Jasmorange, cyclamen aldehyde and Lysmeral ® are members of a family of aldehydes of the formula

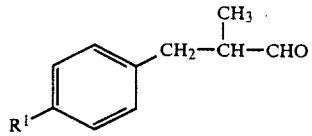

(Jasmorange: $R^1 = -CH_3$; cyclamen aldehyde: $R^1 = -CH-(CH_3)_2$; Lysmeral ®: $R^1 = -C(CH_3)_3$), which are particularly desirable fragrance materials in the perfume industry (cf. Ullmann's Encyclopedia of Ind. Chem., Vol. A1, page 343).

Furthermore, the stated aldehydes as well as the corresponding alcohols and halogen compounds of the formula

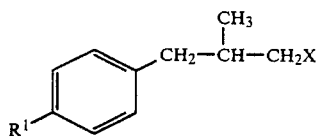

where X is —OH or halogen, are regarded as industrially very important intermediates in the crop protection sector because highly effective fungicides can be prepared by reacting these compounds with morpholine derivatives (cf. Angew. Chemie 92 (1980), 176–181, in particular 179).

A generally applicable synthesis of the above-mentioned compounds, which to date has been the preferred one in industry, starts from the correspondingly substituted benzaldehydes, which are subjected in a first stage to aldol condensation with propionaldehyde to give the corresponding 3-aryl-2-methyl-2-propenals. The latter are then hydrogenated to the corresponding saturated aldehydes or to the corresponding saturated alcohols using catalytically activated hydrogen. Thus, the alkyl-substituted benzaldehydes play a key role in building up the carbon skeleton of the abovementioned popular scents and of the intermediates for crop protection agents.

However, the substituted benzaldehydes are generally produced industrially by oxidation of the corresponding alkylbenzenes, electrochemically, with oxygen or via halogenation, and it is necessary to pass through the oxidation stage of the relevant benzyl alcohol in some form. For this reason, it should be possible to design more economical syntheses of the 3-aryl-2-methylpropanals of the corresponding alcohols and halides if it were possible to extrapolate the principle used for synthesizing the stated compounds to the benzyl alcohols as starting materials.

It is an object of the present invention to provide a simpler and hence more economical method for the preparation of alkyl-substituted phenylisobutyl alcohols and phenylisobutyraldehydes starting from correspondingly substituted benzyl alcohols.

We have found that this object is achieved and that, surprisingly, 3-arylisobutyl alcohols of the general formula I

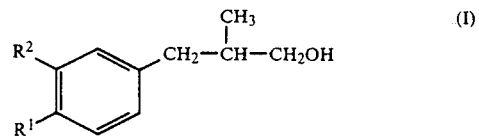

where $R^1$ and $R^2$ are each hydrogen or an alkyl or cycloalkyl radical of not more than 8 carbon atoms, preferably alkyl of 1 to 4 carbon atoms, are obtained in very good yields and in industrially acceptable conversions if the corresponding arylcarbinol of the general formula II

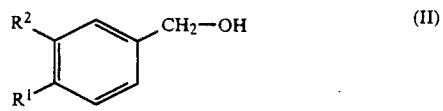

is reacted with n-propanol in the presence of a catalytic amount, ie. about from 0.5 to 2% by weight, based on the reaction mixture, of an alkali metal hydroxide or of an alkali metal alcoholate, preferably NaOH or KOH, in particular KOH, at from 250° to 350° C. in a closed reaction vessel.

It was surprising that the arylisobutanols of the formula I can be obtained by the process described above in excellent yields and with industrially acceptable conversions, even when none of the starting materials is used in excess, ie. the reaction is carried out using a molar ratio of about 1:1 and in the absence of significant amounts of a dehydrogenation catalyst and/or of any other additional catalysts and continuous removal of the water of reaction formed during the reaction is dispensed with.

Although the base-catalyzed condensation reaction of two lower alcohols to give higher alcohols is a reaction which has long been known (Markownikoff-Guerbet reaction; cf. Houben-Weyl, Methoden der Organischen Chemie, 4th edition, Volume VI/1b, Georg-Thieme-Verlag, Stuttgart, New York, 1984, pages 645–652, in particular page 650), the yields obtained are generally very unsatisfactory. The reaction could in general only be carried out in an economical manner if the resulting water of reaction was eliminated continuously from the reaction vessel (cf. loc. cit. page 647), which is particularly important in the prior art when alkali metal hydroxides are used as the basic condensing agent (cf. loc. cit. page 648). This makes the reaction procedure very expensive.

Furthermore, the addition of dehydrogenation catalysts, such as active nickel, copper or copper bromide, and even modification of the dehydrogenation catalysts by means of phosphanes and arsanes and addition of hydrogen acceptors, such as lead salts, have been described for accelerating the reaction and increasing the selectivity (cf. loc. cit. page 648). The disadvantage of this is that removal of the compounds, some of which are harmful to health, complicates the working up of the reaction mixture.

In addition to the dimerization of lower alcohols which is mainly described in the literature (cf. DE 1 443 666, US 2 457 866 and US 3 119 880), cocondensations of two primary alcohols are also known. In loc. cit., page 650, it is stated that benzyl alcohol is very suitable for cocondensations, but, using the method stated there, the 3-phenylisobutanol (referred to there as 2-benzylpropanol) is obtained by reacting benzyl alcohol with propanol in the presence of sodium and copper bronze in an autoclave in a yield of only 32% of theory, which is completely unacceptable industrially. Furthermore, the yields of from 8 to not more than 62%, stated in the Tables on pages 651 and 652 (loc. cit.), for potassium alcoholate-catalyzed cocondensations of alcohols in the presence of active nickel or of copper bronze did not indicate that the desired 3-arylisobutanols of the formula I could be obtained in extremely good yields by simple conversion of the alcohols in the presence of catalytic amounts of an alkali metal hydroxide without further measures which make the reaction more expensive and complicate the working up process.

This is particularly true since, according to loc. cit., the higher yields, such as 62%, could only be obtained by removing water from the reaction mixture, as stated in the Table on page 651.

Particularly suitable arylcarbinols of the general formula II are those in which $R^1$ is alkyl of 1 to 4 carbon atoms and $R^2$ is H. Particular examples are p-methylbenzyl alcohol, p-isopropylbenzyl alcohol and p-tert-butylbenzyl alcohol.

Suitable basic catalysts are alkali metal hydroxides, preferably NaOH and KOH, in particular KOH, and alkali metal alcoholates.

The basic catalysts are used in amounts of from 0.5 to 2, preferably from 0.6 to 1.6, % by weight, based on the reaction mixture, corresponding to about 1-3, preferably about 1.5-2.5, mol %, based on the alcohols.

The reaction temperatures are from 250° to 350° C., preferably from 260° to 290° C.; the reaction times are about 5-12 hours.

The reaction is carried out in a closed reaction vessel because the vapor pressures of the components together in the reaction mixture are above atmospheric pressure.

With the aid of the novel process, the 3-arylisobutanols of the general formula I, which are important as intermediates for the desirable scents jasmorange, cyclamen aldehyde and Lysmeral ® (BASF) or as intermediates for highly effective fungicides, can be obtained in surprisingly good yields in a simple and economical manner. The alcohols of the formula I can be converted into the scents themselves in a simple manner by oxidation with oxygen or by simple dehydrogenation.

EXAMPLES

EXAMPLE 1

A mixture of 2,484 g (23 moles) of benzyl alcohol, 1,380 g (23 moles) of n-propanol and 38 g (0.68 mole) of potassium hydroxide was heated at 270° C. for 10 hours (h) in a 5 l stirred autoclave (material RA2). When the mixture discharged from the reactor was worked up by distillation in a packed column (30 cm packing height, RA2 nets as packing), in addition to unconverted n-propanol and 2-methylpentanol (formed by autocondensation of n-propanol), 1,339 g of unconverted benzyl alcohol and 1,445 g of 3-phenylisobutanol (boiling point 84° C./0.3 mbar) were isolated as the main component. The yield of 3-phenylisobutanol was 91% of theory, based on converted benzyl alcohol, the conversion being about 46%.

EXAMPLES 2 TO 4

A mixture of the alcohols of the formula II and n-propanol in the amounts stated in the Table below and the amount of potassium hydroxide stated there was heated at 270° C. for 15 h in a stirred autoclave. The mixture discharged from the autoclave was worked up by distillation similarly to Example 1. The conversions obtained in this reaction and the yields of alcohols of the general formula I, based on the converted benzyl alcohol of the formula II, are stated in the Table.

TABLE

| Example | Benzyl alcohols (moles) | | n-Propanol (moles) | Catalyst (g) | Isobutyl alcohols of the formula I | Conversion [%] | Selectivity [% of theory] |
| --- | --- | --- | --- | --- | --- | --- | --- |
| 2 | p-Methyl- | (1.0) | (1.0) | KOH (1.8) | 3-(p-Methylphenyl)- | 42 | 93 |
| 3 | p-Isopropyl- | (0.67) | (1.0) | KOH (1.6) | 3-(p-Isopropylphenyl)- | 46 | 92 |
| 4 | p-Tert-butyl- | (14) | (14) | KOH (31.5) | 3-(p-tert-butylphenyl)- | 44 | 92 |

We claim:

1. A process for the preparation of a 3-arylisobutyl alcohol of the formula I

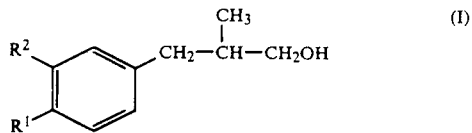

where $R^1$ and $R^2$ are each hydrogen or an alkyl or cycloalkyl radical of not more than 8 carbon atoms, wherein an arylcarbinol of the formula II

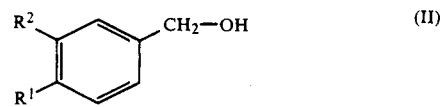

is reacted with n-propanol in the presence of a catalytic amount of an alkali metal hydroxide or of an alkali metal alcoholate at from 250° to 350° C. in a closed reaction vessel.

2. A process as claimed in claim 1, wherein the arylcarbinol of the formula II is reacted with the n-propanol in the presence of from 0.5 to 2% by weight, based on the reaction mixture, of NaOH or KOH.

3. A process as claimed in claim 1, wherein the arylcarbinol of the formula II is reacted with n-propanol in a molar ratio of about 1:1.

4. A process as claimed in claim 1, wherein an arylcarbinol of the formula II

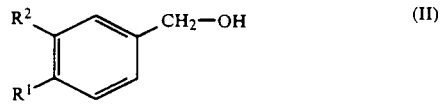

where $R^1$ is methyl, isopropyl or tert-butyl and $R^2$ is hydrogen, is reacted with the n-propanol.

5. A process as claimed in claim 1, wherein the arylcarbinol of the formula II is reacted with the n-propanol in the absence of a dehydrogenation catalyst.

6. A process as claimed in claim 1, wherein the water of reaction formed during the reaction is not distilled off during the reaction of the arylcarbinol of the formula II and the n-propanol.

* * * * *